United States Patent [19]

Soller

[11] Patent Number: 5,582,170

[45] Date of Patent: Dec. 10, 1996

[54] FIBER OPTIC SENSOR FOR IN VIVO MEASUREMENT OF NITRIC OXIDE

[75] Inventor: Babs R. Soller, Northboro, Mass.

[73] Assignee: University of Massachusetts Medical Center, Worcester, Mass.

[21] Appl. No.: 347,875

[22] Filed: Dec. 1, 1994

[51] Int. Cl.$^6$ .............................. G01N 21/27; A61B 5/00
[52] U.S. Cl. .............................. 128/634; 385/12; 356/39; 422/82.09; 436/68
[58] Field of Search .............................. 128/634; 385/12; 356/39; 250/458.1; 422/82.05, 82.09; 436/68, 116, 118

[56] References Cited

U.S. PATENT DOCUMENTS

| | | | |
|---|---|---|---|
| 5,034,189 | 7/1991 | Cox et al. | 436/95 |
| 5,047,208 | 9/1991 | Schweitzer et al. | 128/634 |
| 5,176,882 | 1/1993 | Gray et al. | 128/634 |
| 5,248,616 | 9/1993 | Beckman et al. | 128/632 |
| 5,436,167 | 7/1995 | Robillard | 385/12 |

OTHER PUBLICATIONS

Gabor, G. and Allon, N., "Spectrofluorometric Method for NO Determination", Analytical Biochemistry, 1994, 220:16–19.

Gabor, G. and Allon, N., "Remote Nitric Oxide Detection Employing a Fiber–Optic Sensor", Anal. Biochem., 1994, 220:16, Paper 2388B–78, Session 9.

Kiechle, F. L. and Malinski, T., "Nitric Oxide Biochemistry, Pathophysiology, and Detection", Am. J. Clin. Pathol., 1993, 100:567–575.

Gibaldi, M., 1993, "What is Nitric Oxide and Why Are So Many People Studying it?", J. Clin. Pharmacol. 33:488–496.

Star, R., 1993, "Southwestern Internal Medicine Conference: Nitric Oxide", Am. J. Med. Sci. 306:348–358.

Tanner et al., 1993, "Endothelium–Derived Nitric Oxide, Endothelin, and Platelet Vessel Wall Interaction: Alterations in Hypercholesterolemia and Atherosclerosis", Sem. Thrombosis Hemostasis 19: 167–175.

Shibuki, K., 1990, "An electrochemical microprobe for detecting nitric oxide release in brain tissue", Neurosci. Res. 9:69–76.

Malinski and Taha, 1992, "Nitric oxide release from a single cell measured in situ by a porphyrinic–based microsensor", Nature 358:676–678.

Feelisch and Noack, 1987, "Nitric oxide (NO) formation from nitrovasodilators occurs independently of hemoglobin or non–heme iron", Eur. J. Pharmacol. 142:465–469.

Kikuchi, K. et al., 1993, "Detection of Nitric Oxide Production a Perfused Organ by a Luminol–$H_2O_2$ System", Anal. Chem. 65:1794–1799.

Tracey et al., 1990, "Comparison of Spectrophotometric and Biological Assays for Nitric Oxide (NO) and Endothelium–Derived Relaxing Factor (EDRF): Nonspecificity of the Diazotization Reaction for NO and Failure to Detect EDRF[1]", J. Pharmacol. Exp. Ther. 252:922–928.

Tracey, 1992, "Spectrophotometric Detection of Nitrogen Oxides Using Azo Dyes", Neuroprotocols 1:125–131.

Dave et al., 1994, "Sol–Gel Encapsulation Methods for Biosensors", Anal. Chem. 66:1120A–1127A.

Eguchi et al., 1990, "Optical Detection of Nitrogen Monoxide by Metal Porphine Dispersed in an Amorphous Silica Matrix", Sensors and Actuators B1:154–157.

Robeiro et al., 1993, "Reversible Binding of Nitric Oxide by a Salivary Heme Protein from a Bloodsucking Insect", Science 260:539–541.

(List continued on next page.)

Primary Examiner—Angela D. Sykes
Assistant Examiner—Eric F. Winakur
Attorney, Agent, or Firm—Fish & Richardson P.C.

[57] ABSTRACT

A fiber optic sensor for measurement of in vivo nitric oxide concentrations in a subject. The sensor contains a nitric oxide-sensing compound in a polymer matrix attached to an optical fiber. The sensor may be placed in any blood vessel, including one within the heart of a subject for continuous measurement of nitric oxide concentrations in blood.

27 Claims, 3 Drawing Sheets

OTHER PUBLICATIONS

Feelisch and Noack, 1987, "Correlation between nitric oxide formation during degradation of organic nitrates and activation of guanylate cyclase", Eur. J. Pharmacol. 139:19–30.

Kelm and Schrader, 1990, "Control of coronary vascular tone by nitric oxide", Circulation Research 66:1561–1575.

Kucera, 1990, "Analytical aspects of complex formation between cytochrome C and nitric oxide", Biologia (Bratislava) 45:333–339.

Noack et al., 1992, "Spectrophotometric determination of nitric oxide using hemoglobin", Neuroprotocols 1:133–139.

Sharma et al., 1983, "Reaction of nitric oxide with heme proteins:Studies on metmyoglobin, opossum methemoglobin, and microperoxidase", Biochemistry 22:3897–3907.

Di Iorio, E., 1981, "Preparation of Derivatives of Ferrous and Ferric Hemoglobin", Methods Enzymol. 76:57–71.

Hogg et al., 1992, "Production of hydroxyl radicals from the simultaneous generation of superoxide and nitric oxide", Biochem. J. 281:419–424.

Morris et al., 1992, "Miniature Optical Fiber–Based Spectrometer Employing a Compact Tandem Fiber Probe", SPIE 1796:141–149.

Siegfried et al., 1992, "Cardioprotection and Attenuation of Endothelial Dysfunction by Organic Nitric Oxide Donors in Myocardial Ischemia–Reperfusion [1,2]", J. Pharmacol. Exp. Ther. 260:668–675.

Matheis et al., 1992, "Role of L–arginine–nitric oxide pathway in myocardial reoxygenation injury", Am. J. Physiol. 262:H616–H620.

Hemoglobin +NO

FIG. 1

Cytochrome C+NO

FIBER OPTIC SENSOR FOR IN VIVO MEASUREMENT OF NITRIC OXIDE

BACKGROUND OF THE INVENTION

The present invention relates generally to sensors for nitric oxide in biological systems.

Nitric oxide (NO) has been reported to have important roles in diverse fields, ranging from neuroscience to urology and cardiovascular medicine, and was named "molecule of the year" in 1992 (Koshland (1992) 258:1861–1865). Nitric oxide is known to be produced by the endothelial lining of blood vessels and to be responsible for blood vessel dilation. In cardiovascular medicine, nitric oxide has been implicated in the diseases of hypercholesterolemia, atherosclerosis, and hypertension (Gibaldi (1993) J. Clin. Pharmacol. 33:488–496; Star (1993) Am. J. Med. Sci. 306:348–358; Tanner et al. (1993) Sem. Thrombosis Hemostasis 19:167–175). It has also been shown that large quantities of nitric oxide are produced during massive infection, and may be responsible for septic shock, a common complication of post-surgical patients.

Biological measurements of nitric oxide have been reported in cultured cells or isolated perfused organs. Nitric oxide has only been measured in human subjects indirectly, through stimulation or inhibition of substrates and enzymes involved in nitric oxide production.

Fiber optic sensors have been used to measure oxygen, carbon dioxide, and the pH of blood inside an artery. A fiber optic sensor has been used for measuring nitrogen oxide in the atmosphere; however, this sensor is not sufficiently sensitive to detect nitric oxide concentrations in biological systems.

Two types of electrochemical sensors have been described for nitric oxide. Shibuki (1990) Neurosci. Res. 9:69–76, developed an electrode based on a modified oxygen electrode for measurement of NO concentrations less than 100 nM in brain tissue. The linear range of the Shibuki electrode is between 1–3 $\mu$M. Because of the frequent calibration required by oxygen electrode-type sensors, a NO electrode based on this technology is not suitable for in vivo continuous monitoring in a biological system.

Malinski and Taha (1992) Nature 358:676–678, developed a sensor which measures current or voltage resulting from the electrochemical oxidation of NO to the nitrite ion $NO^{-2}$ catalyzed by a polymeric metalloporphyrin. The Malinski sensor is very small, composed of a fragile carbon fiber which allows measurement of NO in a single cell. Malinski and Taha report a detection limit of 10 nM with a linear response up to 300 $\mu$M and a response time of 10 msec.

Optical methods have been previously developed for measuring NO concentration in cell cultures and perfusate from isolated organs. Chemiluminescence has been used to detect NO by its reaction with ozone (Feelisch and Noack (1987a) Eur. J. Pharmacol. 142:465–469) or luminol-$H_2O_2$ (Kikuchi et al. (1993) Anal. Chem. 65:1794–1799) to produce light emission. Although a sensitive technique, methods of chemiluminescence detection cannot be readily adapted for use in a fiber optic sensor because they require the addition of an analyte in order to generate light.

The diazotization assay is a spectrophotometric assay which measures nitric oxide through its conversion to the nitrite ion. This assay is not suitable for measurement of NO in a biological system because it is not specific for NO since nitrites are also produced from other sources (Tracey et al. (1990) J. Pharmacol. Exp. Ther. 252:922–928). Further, the detection limit is about 0.2 to 2.0 $\mu$M (Tracey (1992) Neuroprotocols 1:125–131).

Suggested methods for immobilizing biomolecules include covalent binding, physical adsorption, or crosslinking to a suitable carrier matrix, and physical entrapment and microencapsulation in a polymeric or $SiO_2$ matrix (sol-gel) (Dave et al. (1994) Anal. Chem. 66:1120A–1127A). The use of hemes and porphyrins immobilized by the sol-gel method have been investigated in the development of NO sensors. For example, Eguchi et al. (1990) Sensors and Actuators B1:154–157 investigated various metal ion-doped porphyrins immobilized onto the end of a fiber for the measurement of nitric oxide from combustion products. They found that Co-doped porphyrin was most sensitive to nitric oxide in the range of 10–1000 $\mu$M at 200° C. Eguchi et al. monitored the change in optical absorption at 420 nm, attributing this change to the oxidation of Co(I) and the formation of Co(II)-NO complex. Dave et al. (1994) supra report the use of sol-gel immobilized manganese myoglobin for measurement of NO.

SUMMARY OF THE INVENTION

The invention features a sensor device for measuring the in vivo concentration of nitric oxide (NO) in a subject. The NO-sensing device includes an NO-sensing compound immobilized in a fiber optic sensor. The NO-sensing compound reacts with NO in the biologically relevant range of 0.001–10.0 $\mu$M, and the reaction results in the generation of a measurable chemical reaction product. The amount of the chemical reaction product is proportional to the in vivo NO concentration. The sensing device of the invention is useful for continuous monitoring of NO concentrations in the blood vessel of a subject.

Included in the invention are methods and procedures for testing and identifying candidate compounds for use as NO-sensing compound in the fiber optic sensor of the invention. These methods and procedures include determining the absorption spectra of the compounds in an aqueous buffer solution in the absence and presence of NO. Compounds sensitive to NO are tested for NO selectivity by measuring their absorption spectra in the presence of blood. Compounds exhibiting sensitivity and selectivity to NO are imbedded in a polymer matrix film or plug which is incorporated into the fiber optic sensor system of the invention.

The NO-sensing compounds used in the sensor of the invention may react reversibly or irreversibly with NO. In one embodiment of the invention, the NO-sensing compound used in the sensor is a metal-containing compound selected from the group of compounds containing iron, manganese, cobalt, platinum, osmium, and ruthenium. For example, iron-containing compounds suitable for use in the sensor of the present invention include hemes, e.g., selected from the group consisting of oxyhemoglobin, cytochrome c, hemin, and myoglobin.

In one embodiment, the NO sensor of the invention includes a dual chamber catheter containing two fibers, each fiber having an angled mirror end, a transparent plug between the mirror ends of the fibers, a light source, and light detector. NO-sensing compound imbedded in a polymer matrix is contained in a section of the fiber transmitting light to the detector. NO permeates to the NO-sensing compound through an opening in the catheter.

The fiber optic sensor of the present invention provides a number of important advantages over prior art NO sensors.

It is sufficiently small and sturdy to be inserted into the femoral artery of a subject or placed within a coronary artery of a beating heart. Further, it is free of the drift problems associated with prior art electrochemical sensors, and therefore, is suitable for use for long-term continuous monitoring applications (e.g., 72 hours or more). The sensor of the present invention allows in vivo measurement of nitric oxide production in diseased coronary arteries and NO monitoring in patients in septic shock.

Other features and advantageous of the invention will be apparent from the following description of the preferred embodiments thereof, and from the claims.

DETAILED DESCRIPTION

The fiber optic sensor of the present invention allows direct measurement of in vivo NO production in intact subjects. The present invention is sufficiently sturdy and stable to allow continuous NO monitoring over prolonged periods of time.

The invention can employ any of a wide variety of known nitric oxide sensing compounds, e.g., hemoglobin, cytochrome c, manganese myoglobin, and metal containing compounds whose optical properties change upon reaction with nitric oxide, such as many metal-centered hemes and phorphyrins.

Example 1 below describes the development of the nitric oxide sensor of the present invention. A protocol has been developed and is described below which allows testing and identification of NO-sensing compounds suitable for use in the NO sensor for detecting biological levels of NO. In the example, NO-sensing compounds tested are heme compounds. NO is highly reactive with hemes which have a number of optical transitions that can be adapted for sensing. These heme compounds include Fe(II), which is readily oxidized to Fe(III) by NO and can be monitored by absorption spectroscopy. Additionally, Fe(III) forms a stable complex with NO, Fe(III)-NO, resulting in the appearance of a new absorption band. The present invention involves a device able to detect NO with a NO-sensing compound whose optical properties change as a function of NO concentration. Detailed instructions and guidance, as well as examples, are provided below for testing and identifying NO-sensing compounds. NO-sensing compounds suitable for use in the sensor of the invention include naturally occurring hemes, such as hemoglobin, myoglobin, and cytochrome c. For example, the salivary heme protein from *E. prolixus* may be tested for its suitability for use in the NO sensor (Ribeiro et al. (1993) Science 260:539–541). Also suitable as NO-sensing compounds are plain or substituted porphyrins containing manganese, iron, cobalt, or ruthenium, for example, hemin. NO-sensing compounds suitable for use in the NO sensor of the invention are not limited to these compounds. With the detailed guidance provided herein, any candidate compound may be tested by the protocol described below to determine its suitability for use in a NO sensor.

Initially, candidate compounds are characterized by their absorption spectra in an aqueous buffered solution. The candidate compound is then placed in solution in the presence of a NO-generating compound, such as 3-morpholinosydnonimine-N-ethylcarbanide (SIN-1) or diethylamine NONOate (DEAN), and the absorption spectra determined. The ability of the candidate compound to respond to NO is compared to that of the standard, oxyhemoglobin. Candidate compounds responsive to NO are then tested for their ability to respond to NO in blood (NO selectivity).

Compounds with high sensitivity and selectivity for NO are then combined in a polymer matrix by formation of a film or plug. The spectral characteristics of the films or plugs are then tested in an aqueous buffered solution and blood, in the presence and absence of a NO-generating compound. The stability of the NO-sensing compound in the polymer film or plug is then tested by continuous measurement over a period of time, and degradation in sensitivity to NO determined.

Nitric Oxide Sensors.

Hemes and Porphyrins. Hemes and porphyrins have a rich chemistry based on the spectra of their metal ion centers and their high reactivity with NO. A spectrophotometric assay based on oxyhemoglobin has been described (Feelisch and Noack (1987b) Eur. J. Pharmacol. 139:19–30; Kelm and Schrader (1990) Circulation Research 66:1561–1575; Noack et al. (1992) supra). The oxidation of oxyhemoglobin by NO to methemoglobin produces a measurable shift in the adsorption spectrum from 415 nm to 401 nm, due to the oxidation of Fe(II) to Fe(III). The hemoglobin traps NO within 100 msec, providing a rapid response time. Feelisch and Noack (1987b) supra have shown that their assay is selective for NO in the presence of oxygen and nitrites, and can detect NO production to a level of 0.2 nmol/min. Kelm and Schrader (1990) supra have shown that NO concentrations in the range of 1–100 nM are most significant for coronary artery dilation in a perfused heart model and that these levels are detectable by the hemoglobin-based spectrophotometric assay.

The spectrophotometric determination of NO by its formation of a complex with cytochrome c, an Fe(III) heme, is sensitive and specific to NO (Kucera (1990) Biologia (Bratislava) 45:333–339). In the presence of NO, cytochrome c forms a complex whose appearance can be monitored by absorption spectroscopy at 563 nm. This assay has been shown to be sensitive to NO levels of 15 nmoles.

Fiber Optic Sensors

NO-sensing compounds are incorporated into a suitable fiber optic sensor system. The system is optimized for sensitivity to NO under biological conditions, by such features as a long path length absorber and the possible inclusion of a light source at the end of the optical fiber.

The sensor of the present invention is useful as a clinical diagnostic tool to monitor the progression of heart disease. For example, diminished NO production by blood vessels has been implicated in atherosclerosis. Further, high levels of NO have also been detected in patients with septic shock and may precede a drop in blood pressure. The sensor of the present invention may be used to continuously monitor NO production in patients with septic shock as a means of anticipating and preventing a dangerous drop in blood pressure.

The following examples are offered by way of illustration and not by way of limitation.

EXAMPLE 1

The Nitric Oxide Sensor.

A previously-developed hemoglobin-based in vitro assay system for NO in which NO induces oxidation of oxyhemoglobin Fe(II) to methemoglobin Fe(III) (Noack et al. (1992) Neuroprotocols 1:133–139) was adapted for use in the NO sensor of the present invention. Myoglobin was studied to determine its suitability as an NO-sensing compound. Myoglobin was chosen because it is known to form a stable complex with NO (Sharma et al. (1983) Biochemistry 22:3902–3907).

After the spectra of the standard and candidate compounds and its sensitivity to NO are established in an aqueous buffered solution, selectivity for NO in the presence of blood is determined.

Standard NO sensitivity.

Oxyhemoglobin was tested for use as a standard NO-sensing compound. The initial oxyhemoglobin tested was a mixture of oxyhemoglobin, deoxyhemoglobin, and methemoglobin. The Fe(III) compound is reduced with dithionate and filtered using a Sephadex G-25 column to produce the Fe(II) heme (Di Iorio (1981) Methods Enzymol. 76:57–71). Oxyhemoglobin was characterized by measuring its absorption spectra in an aqueous buffered solution (pH 7.4) at room temperature. The Fe(II) spectra is measured under conditions in which the reduced compound is free from air and light. The ambient oxidation of Fe(II) to Fe(III) is then monitored to determine the stability of the reduced compound and to measure the spectral properties ($\lambda_{max}$, $\epsilon$) of the oxidized species Fe(III). Finally, the Fe(II) compound is reacted with fixed amounts of NO to form the Fe(III) species and the Fe(III)-NO complex. NO was produced by 3-morpholinosydnonimine N-ethylcarbanide (SIN-1), an organic nitric oxide donor which generates NO at an estimated rate of about 1 µM/min at room temperature. SIN-1 is an appropriate model for the continuous release of NO that occurs in vivo because it releases NO at a rate of approximately 3 µM/min at 37° C. (Hogg et al. (1992) Biochem. J. 281:419–424). Two solutions containing the same concentrations of oxyhemoglobin (HbO$_2$) were placed in the sample and reference compartments of a dual-beam spectrophotometer. SIN-1 (1 mM) is injected into the sample cuvette and NO released at a continuous rate. The difference in absorbance between 401 nm (methemoglobin, Hb$^+$) and 411 nm (isosbestic point of the HbO$_2$ and Hb$^+$spectra) is monitored continuously and used to calculate the rate of NO release at room temperature. This rate is used as a standard for comparison with other candidate compounds.

Figure 1:
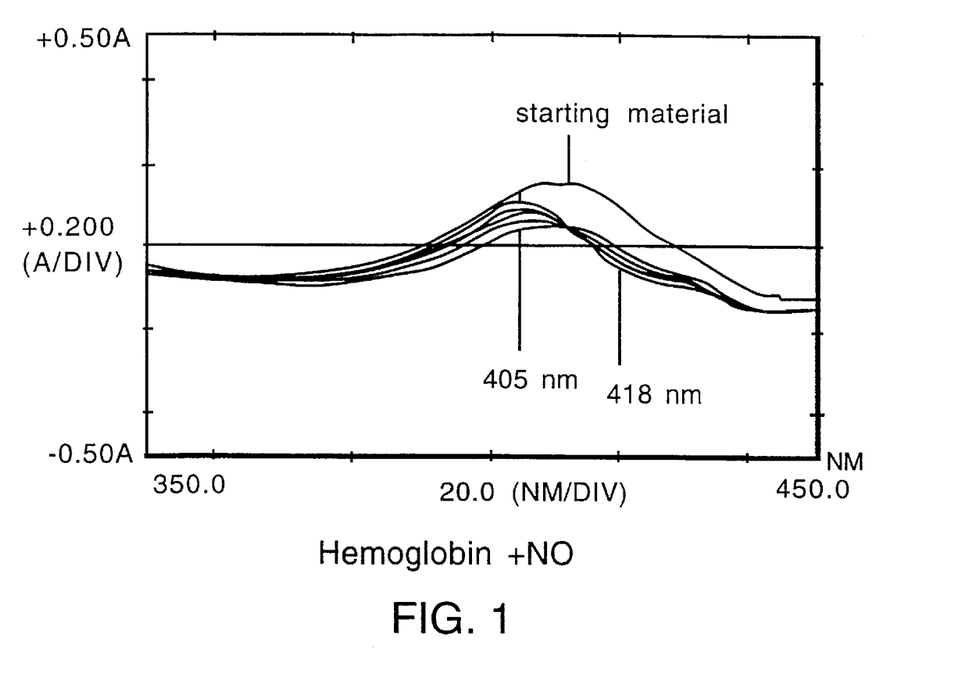
FIG. 1 is a graph illustrating the difference spectra of a hemoglobin solution exposed to nitric oxide.

The NO-induced oxidation of Fe(II) to Fe(III) was monitored by difference spectroscopy once per minute over a 7 minute period. The absorption maxima of these species was determined and followed over time to determine stability. The difference spectrum was measured in the wavelength range of 350 nm to 450 nm, and shows the results in absorbance when NO is added oxyhemoglobin minus the absorbance of hemoglobin itself, and is a sensitive method for detecting small changes in NO concentration. The absorption peak at 405 nm increase and absorption at 418 nm decrease as methemoglobin is produced from oxyhemoglobin (FIG. 1). Although the starting material was not pure hemoglobin, changes in the spectra due to generation of NO were resolvable. In the 7 minute reading, the sensor was able to detect a 2-fold change in absorbance of the methemoglobin peak due to the production of NO.

Cytochrome c was tested for use as a standard NO-sensing compound, based on cytochrome c-NO complex formation in a poly(vinyl alcohol) (PVA) solution. Solutions of cytochrome c were prepared in aqueous solutions of PVA (2% w/v, pH 7.2) in sealed 1 cm cuvettes. Into each cuvette was injected a specific amount of diethylamine NONOate (DEAN, Cayman Chemical). Each mole of DEAN produces 1.5 moles of NO. The concentration of DEAN was determined spectrophotometrically in a separate cuvette by monitoring absorbance at 250 nm.

Figure 2:
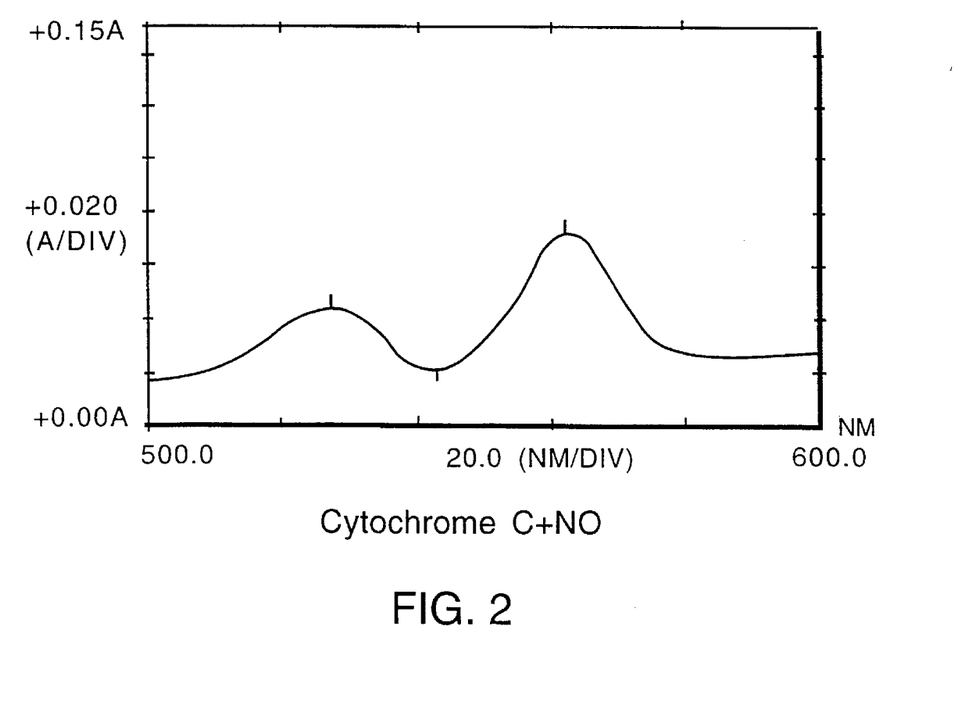
FIG. 2 is a graph showing the difference absorption spectrum of cytochrome c-NO complex at 562 nm after 99 nmoles NO is added to the cytochrome c solution. No absorption at 562 nm is seen prior to addition of diethylamine NONOate (DEAN).
Figure 3:
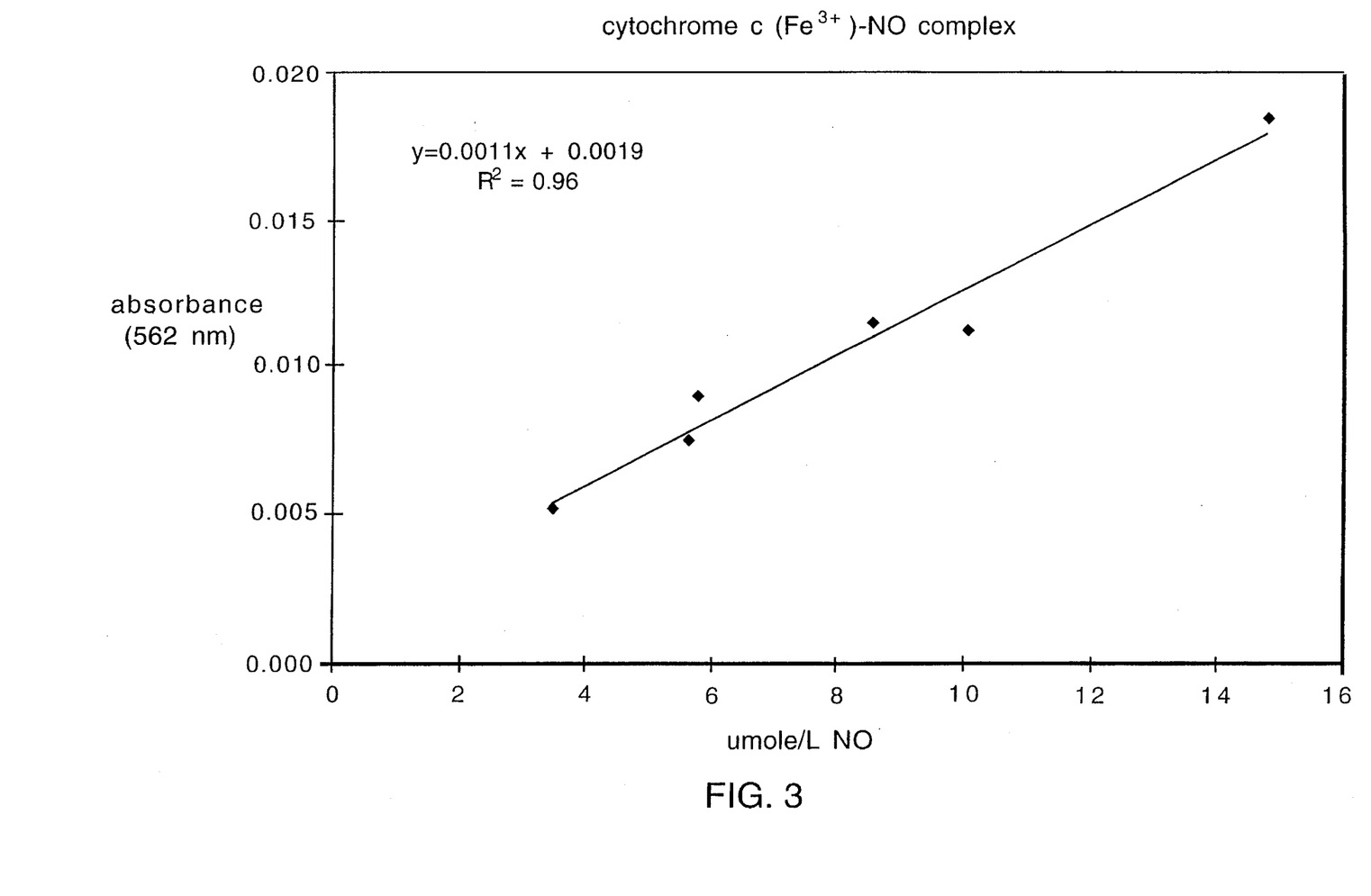
FIG. 3 is a graph describing the linear relationship between absorbance by the cytochrome c-NO complex and NO concentration.

The formation of the cytochrome c-NO complex was monitored by difference spectroscopy at 562 nm (FIG. 2). Two cuvettes with identical concentrations of cytochrome c were placed in the sample and reference compartments of a dual-beam spectrometer. DEAN was injected into the cuvette in the sample compartment and the absorbance at 562 nm measured over a 6 min period during which all of the DEAN was reacted. In order to compare sensor compounds, a calibration curve is generated (FIG. 3). The slope of the line (change in absorbance divided by change in NO concentration) is a measure of NO sensitivity. FIG. 3 shows the calibration curve generated from spectra similar to that shown in FIG. 2. These results establish that cytochrome c suspended in the polymer poly(vinyl alcohol) is sensitive to NO at concentrations less than 5 µM. The slopes obtained for different hemes or phorphyrins in aqueous solutions or the same compound in different polymer solutions or matrices can be compared to obtain an indication of relative sensitivity to NO. The value of NO concentration at the absorbance level which is the minimum detected absorbance of the spectrophotometer or sensor optical system is the minimum detectable amount of NO for the compound under study.

NO sensitivity of candidate compounds.

The response of test compounds to NO is determined using the procedure described above. If other compounds are less responsive to NO, the measured rate of NO production will be lower.

NO selectivity of candidate compounds.

Since the measurements of NO will be made in blood, it is necessary to evaluate candidate compounds for the ability to detect NO in the presence of blood, e.g., selectivity for NO. The above experiments are repeated by replacing the aqueous buffered solutions with fresh canine or human blood, and the relative rate of response to NO measured. These results are compared with the results obtained with oxyhemoglobin in aqueous solution, and compounds with the greatest response to NO and highest stability against oxidation selected.

In order to interface selected compounds with an optical fiber, the compounds are contained in a polymer matrix. The matrix must be transparent in the wavelength region of interest and be highly permeable to NO. Candidate polymers having the required properties and varying in permeability to NO include NAFION® brand tetrafluoroethylene-sulphonyl-fluoride vinyl ether copolymer, polymethyl methacrylate (PMMA), polyhydroxyethylmethacrylate (PHEMA), and polyvinyl alcohol (PVA). NAFION® is a fluorinated material which has been used as a membrane for electrochemical NO sensors and has a high NO permeability. PMMA is also highly permeable to gaseous molecules and forms good films. PHEMA has been used to provide more hydrophilic films and gels with high permeability of gases. PVA has been used with chemical cross-linking as a support for immobilized enzyme systems with high permeability and a high surface area through the formation of thin fibers. After spectral characteristics of the compounds are obtained to assure transparency, candidate NO-sensing compounds are incorporated into films. Films are formed by casting a solution of the compound on the wall of a spectrometer cuvette and allowing a film to form by slow evaporation of the solution.

The absorption spectra of the Fe(II) and Fe(III) species and the Fe(III)-NO complex is measured in the films. It is expected that "solvent effects" of the polymer will shift the $\lambda_{max}$ and possibly alter the molar extinction coefficient ($\epsilon$) of the compounds. The response to NO is measured using SIN-1 as described above, in aqueous buffered solutions and blood, and the results compared with the standard measurement obtained with hemoglobin in aqueous buffered solution. This determination is used to select heme-polymer combinations with the required sensitivity to NO.
Evaluation of stability.

The stability of the NO-sensing compound immobilized in a polymer matrix is determined by measuring the spectra of the film immersed in physiological buffer for several hours. The absorbance maxima is measured continuously for 4 hours and any degradation of the signal monitored. Degradation may be due to either photobleaching or to leaching of the NO-sensing compound from the polymer matrix. The spectra of a new sample is recorded every 10 minutes during the 4 hour period to minimize the exposure of the compound to light. If it is determined that light exposure results in degradation of the absorbing species, the fiber optic system can be designed to operate in the pulse mode to minimize light exposure. If it is determined that leaching is a problem, methods of covalently binding the sensor compound to the polymer matrix known to those skilled in the art will be applied. Another method of preventing leaching is to cross-link the polymer to form smaller pores to trap the sensing compound.

The above described methodology results in selection of sensor compound most sensitive to NO in blood and most stable under the physiological conditions of its use.
Optical and Data System.

A flexible and modular optical system is required for development of the absorption-based sensor of the invention. Such a system can deliver light into an optical fiber to excite the sensor, efficiently collect the returned light, and convert it to NO concentration. As needed, signal processing may be incorporated into the system to eliminate system noise or background. The optical system may also be used with fluorescent or phosphorescent sensors under conditions in which luminescent sensors are to be used.

In specific applications, the optical system would consist of diodes at specific wavelengths and no grating. In a general description of one system (Ocean Optics System), the components of the optical system (Ocean Optics) are optimized for fiber optic output from the light source and fiber optic input to the detector (Morris et al. (1992) SPIE 1796:141–149). These components, connected by SMA connectors, include:

(1) Fibers. 100 μm silica core, silica clad fibers are used in the optical system.

(2) Light source. The sensor design utilizes a continuous tungsten halogen lamp. This lamp may be replaced with a pulsed source or a chopper may be placed in front of the lamp under conditions where photodegradation of sensor compounds is determined to occur, or under conditions where synchronization of the source and detector is desirable to filter out background noise.

(3) Detector. A 1200 lines/mm grating over the range of 400–650 nm disperses light onto a 1024 element CCD detector with a resolution of approximately 1–2 nm. This level of resolution is adequate for most expected uses of the NO sensor. If improved resolution is required, the grating may be changed, or the diameter of the fiber which goes to the detector and acts as the entrance slit of the spectrometer may be reduced.

(4) Data system. The detector is connected to a PC through a National Instruments A/D board. The spectrometer and acquired data is driven by Spectrasoft software (World Precision Instruments). This software, based on the LabView software, is used to determine the best method of reading data from the CCD to achieve the desired sensitivity. For example, signal/noise ratio may be altered by use of LabView software signal processing algorithms if necessary. LabView software may also be used to perform sensor calibration and display real-time values of NO concentrations. Noack et al. (1992) supra reported a theoretical detection limit for NO of about 2.8 nM based on the oxyhemoglobin assay. Using the molar extinction coefficient (36 mM$^{-1}$ cm$^{-1}$), this translates into the ability to measure a change in absorbance equivalent to 0.0001 absorbance units. Proper sensor design and signal processing in the above described optical system allows this sensitivity to be achieved.

Sensor fabrication techniques and evaluation of sensor performance.

With the use of the fiber optic monitoring system, the physical design of a sensor may be evaluated for efficiency in returning light from the sensor to the detector, sensitivity, response time, stability, and reproducibility.

Figure 4:
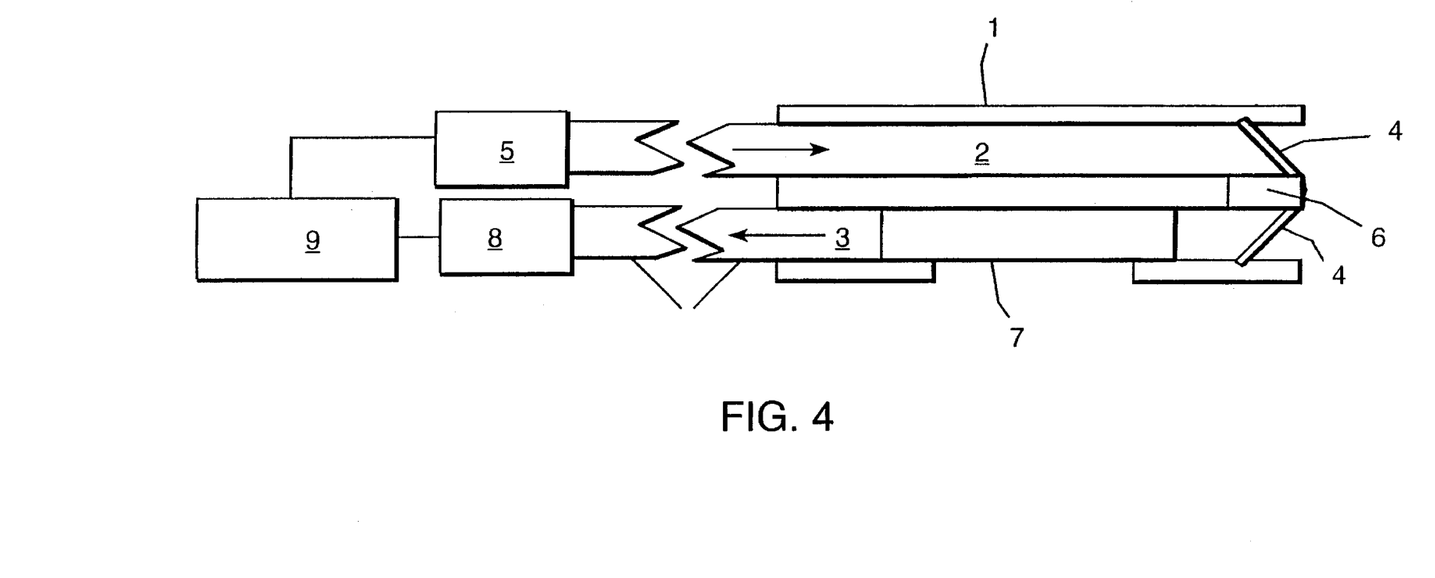
FIG. 4 is a schematic representation of one embodiment of the nitric oxide sensor of the invention.

One embodiment of the sensor design is shown in FIG. 4. Dual lumen catheter 1 include two fibers 2 and 3. The catheter has an outer diameter less than 1 mm as a housing for the two fibers. The distal ends of each fiber are cut and polished at a 45 degree angle, and aluminum or gold evaporated onto the polished surface to form mirrors 4. Fiber 2 transmits light from the source 5 to the mirrored end 4. The mirrored end 4 of fiber 2 reflects light through the transparent plug 6 to fiber 3. A small section of fiber 3 is removed for incorporation of the NO-sensing compound 7. Light travels from the source 5 through fiber 2, is reflected by the mirrored end 4 through the transparent plug 6 to fiber 3, and through the NO-sensitive compound 7 to a detector 8. Light output and input are processed by computer 9.

The length of the section removed from fiber 3 is a control for the path length of the absorbing compound, and can be varied as needed to optimize sensor performance. The NO-sensing compound is injected into a mold containing the catheter and allowed to cure, forming a semi-rigid NO-permeable plug. The fiber with the second mirror is aligned before the gel is cured and fixed in place. Prior to assembly, a portion of the sidewall of the catheter is removed to allow NO gas to permeate to the sensing compound. A notch is removed from the center of the catheter to form a gap for light to be reflected between the two fibers. The gap is filled with a plug of transparent compound.

Figure 5:
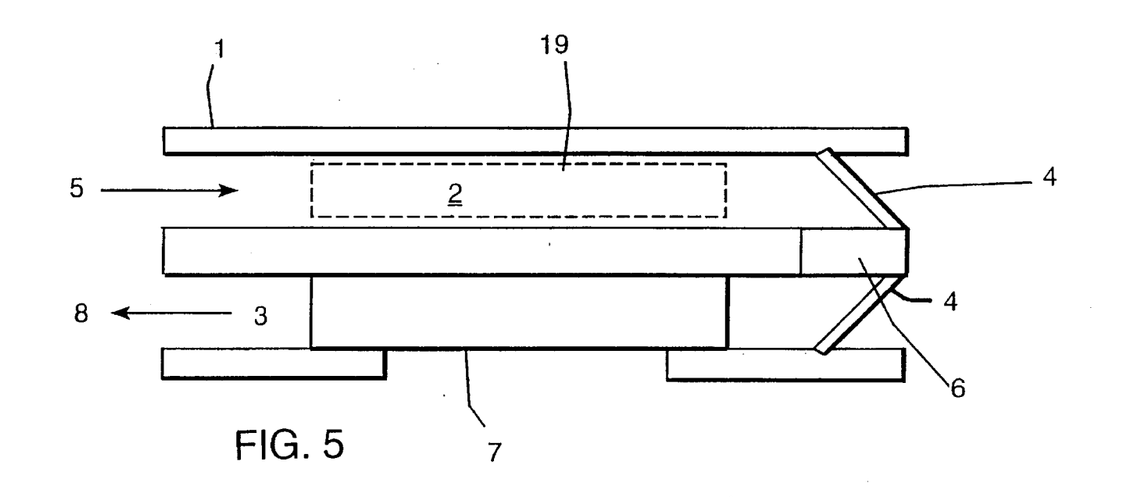
FIG. 5 is a schematic representation of one embodiment of the nitric oxide sensor of the invention. having a reference compound in the pathlength of the incoming fiber.

The sensor of the present invention has three unique features that allow it to be tailored for optimal performance. First, the sensor is designed to have a long path length absorber. These dimensions are controlled during the manufacturing process. This feature provides an advantage over dip-coated sensors where the path length is usually very small (50–100 μm) and difficult to control in manufacturing. The second feature of the dual-fiber sensor of the present invention is the presence of the gap between the two fibers. The sensor is initially operated with a transparent plug between the two mirrored surfaces. The transparent plug is made from the same polymeric material as the absorber, but without the NO-sensing compound. If insufficient light is returned to the detector, the design of the sensor may be modified to replace the transparent plug with a plug that emits light. For example, a luminescent compound may be used in that space which will be excited by the light source. The light emitting compound is selected to luminesce at the same wavelength as the absorbance of the sensing compound. The presence of a strong light source at the fiber end may be used to increase detector response if required. A third feature is the ability to include a reference compound in the pathlength of the incoming fiber. This option is illustrated in FIG. 5 19. This feature essentially allows use of dual-beam spectroscopy, and avoids the need to mathematically correct for changing optical properties of the sensor compound.

Chemical and mechanical procedures are used for assembling the sensor. The effectiveness of these procedures are evaluated by measuring the intensity of transmitted light. It is an aim of the present invention to maximize the intensity of transmitted light by accurately aligning the pieces of fiber with the mirrored surface and the plug of sensor compound with the incoming and outgoing fibers.

When sufficient light is determined to reach the detector, the performance of the sensor is evaluated by measuring sensitivity to NO in aqueous buffered solutions and blood, response time, stability from drift, and reproducibility of manufacture. These parameters are determined essentially as described above. Sensitivity to NO is determined by use of the SIN-1 method developed for evaluation of aqueous solutions and films. The response to release of NO by SIN-1 is measured and compared to the standard measurement of an aqueous oxyhemoglobin solution. The measurement is repeated in blood to determine sensor selectivity. The detection limit for NO is calculated. The response time of the sensor is determined by placing the sensor in aqueous solution containing a fixed amount of NO, and the time for the sensor to reach equilibrium measured. Response time is calculated as the time required to reach 90% of full scale response. The target response time is in the range of a few seconds; however, sensors with response times of a few minutes will be valuable for measurement of stable levels of NO concentration. The stability of the sensor signal is determined in the absence of NO. An ideal sensor will have a baseline variability of less than 5% over a 4 hour period. Finally, the ability to reproducibly manufacture the sensors is determined. This requires that sensors be produced with reproducible characteristics of NO sensitivity, response time, and stability.

Sensor calibration methods and modeling equations.

Calibration equations and procedures are required to relate the optical properties of the NO sensing compound to the acquired signal. To calibrate the sensors, equations are derived to relate transmitted light intensity to NO concentration. Light is collected at two wavelengths, the wavelength at which absorption changes as a function of NO concentration, and a wavelength that is insensitive to NO (reference wavelength). The reference wavelength may either be the isosbestic point for all absorbing species or a wavelength at which none of the species absorb. Collecting light at the reference wavelength serves to normalize the signal for changes in the optical system such as fluctuations in light intensity, detector response, and fiber bending. In the simplest case, in the case of a $Hb^+$-based sensor, the sensor obeys the modified Beer's law relationship described by equations 1 and 2:

$$\log S = \log (I_R/I) = \epsilon l\, [Hb^+] + I_O \qquad \text{Eq. 1}$$

or $$S = I_R/I = k \times 10^{\epsilon l [Hb+]} \qquad \text{Eq. 2}$$

where S is the measured sensor signal, the ratio of transmitted light at the reference and sensing wavelengths, $\epsilon$ is the molar extinction coefficient for the absorbing heme ($Hb^+$ in this example), I is the path length, $[Hb^+]$ is the methemoglobin concentration (equal to the concentration of NO), and $I_O$ and k are constants related to the incident light intensity at the two monitored wavelengths. An exact value for these constants are derived from the sensing compounds in the completed sensor.

Multiple absorption peaks may occur when several competing reactions occur simultaneously. For oxyhemoglobin ($HbO_2$), the formation of methemoglobin ($Hb^+$) from the oxidation of $HbO_2$- by NO must be monitored. This reaction competes with the autoxidation of $HbO_2$ to form methemoglobin. With sensors based on the oxidation of Fe(II), a mathematical correction for the autoxidation of the Fe(II) species is determined. This is done by measuring the autoxidation rate of the heme-polymer complexes over a range of physiological conditions: the temperature range between 35°–40° C., pH range between 7.2–7.4, $pCO_2$ range between 30–40 mm Hg, and $pO_2$ range between 70–150 mm Hg. Under conditions in which the rate is strongly correlated to temperature, a thermocouple is included with the sensor. Under conditions where the rate is independent of blood gas parameters, autoxidation is mathematically corrected. The sensor design may also be modified to include a second plug of sensor compound that is not exposed to NO. The autoxidation of the unexposed sensor compound is monitored directly by the sensing system as an internal correction.

After derivation of the appropriate equations relating NO concentration to the sensor signal S, the sensor is calibrated. Calibration ranges will depend on the application of the sensor. For example, for measuring low levels of NO, calibration would range between 1–100 nM NO. For septic shock application, calibration would likely range between 0.1–10 μM NO. Calibration is conducted by measuring 5 different aqueous solutions of gaseous NO in the appropriate concentration range. The equations are fitted to the data points, and an $r^2$ (correction coefficient) determined. A satisfactory calibration equation is defined as having an $r^2$ value >0.9.

The most critical parameter of the sensor of the invention is sensitivity to NO concentration ($dS/d[NO]$). The sensitivity equation is derived from the calibration equation (equation 2). Sensitivity depends on the path length of the sensor 1, the concentration of the absorbing species, and $\epsilon$, the molar extinction coefficient for the absorbing species. $\epsilon$ is a property of the absorber-polymer mixture, and not easily altered. However, the path length and the concentration of absorber are easily controlled during manufacture. From the known sensitivity equation, the factors which are most likely to improve sensitivity to NO may be determined. Sensors are then made with varying concentrations and path lengths, as appropriate, to reach target sensitivities of <10 nM NO and resolutions of 1–2 nM.

EXAMPLE 2

Measurement of In Vivo Nitric Oxide.

The calibrated sensor produced by the method described in Example 1 is used to detect NO production in a dog artery.

Five dogs (22–30 kg) are anesthetized with intravenous sodium pentothal (20 mg/kg), and mechanically ventilated with halothane anesthesia (1–2%) maintaining normal arterial gas tensions and pH. Surface ECG sensors are used to monitor heart rate. Both the right and left femoral arteries are exposed, and a flow probe (Transonics) place around each vessel. NO sensors are placed directly into the femoral arteries of both legs. The sensor in one leg is used as a control. Baseline levels of NO are monitored for 30 minutes. SIN-1 is then infused (1 mg/kg) into one leg for 10 minutes and responses determined with the NO and blood flow sensors. SIN-1 has previously been successfully used to generate NO in the coronary arteries of cats (Siegfried et al. (1992) J. Pharmacol. Exp. Ther. 260:668–675). The NO sensor in the SIN-1 leg responds rapidly to the release of NO with a simultaneous observed increase in blood flow. The sensor in the control leg shows no response. After a 30 min stabilization period, the sensor is tested with an endogenous source of NO. Bradykinin is used to stimulate endothelial production of NO. Kelm and Schrader (1990) supra showed that 100 nM bradykinin increased NO release 3-fold over basal levels in isolated guinea pig heart. Bradykinin is infused for 10 min and NO and blood flow monitored. Bradykinin infusion will be increased until a significant change in blood flow is observed. NO sensor responses in both legs are compared. After another 30 min stabilization period, NO concentration is increased with either SIN-1 or bradykinin infusion for 10 min. This is immediately followed by administration of $N^G$-nitro-L-arginine methyl ester (L-NAME, 4 mg/kg) for 10 min. L-NAME is a strong inhibitor of endothelial NO synthase (Matheis et al. (1992) Am. J. Physiol. 262:H616–H620). The NO sensor registers a decrease in NO production in response to L-NAME.

Other embodiments are within the following claims.

What is claimed is:

1. A device for measuring an in vivo amount of nitric oxide, comprising:

a nitric oxide-sensing compound; and an optical system comprising optical fibers arranged to deliver light to and collect light from said nitric oxide-sensing compound;

wherein said nitric oxide-sensing compound reacts with nitric oxide in vivo to induce a change in an optical property of said nitric oxide-sensing compound by an amount proportional to the in vivo amount of said nitric oxide.

2. The device of claim 1, wherein said nitric oxide-sensing compound is a metal-containing compound.

3. The device of claim 2, wherein said metal-containing compound contains iron, manganese, cobalt, platinum, osmium, or ruthenium.

4. The device of claim 1, wherein said nitric oxide-sensing compound is oxyhemoglobin.

5. The device of claim 1, wherein said nitric oxide-sensing compound is cytochrome c.

6. The device of claim 1, wherein said nitric oxide-sensing compound is hemin.

7. The device of claim 1, wherein said nitric oxide-sensing compound is myoglobin.

8. The device of claim 1, wherein said device further comprises a light source for delivering light through said optical system to said nitric oxide-sensing compound, and a light detector for generating an electrical signal in response to light which passes through said nitric oxide-sensing compound or is emitted from said nitric oxide-sensing compound.

9. The device of claim 8, further comprising a processor for analyzing the electrical signal to determine the in vivo amount of nitric oxide.

10. The device of claim 1, wherein said optical system comprises a first optical fiber for delivering radiation to said nitric oxide-sensing compound, and a second optical fiber for collecting radiation which passes through said nitric oxide-sensing compound.

11. The device of claim 10, wherein said second optical fiber contains first and second portions which are separated to form an opening.

12. The device of claim 11, wherein said nitric oxide-sensing compound is disposed in said opening.

13. The device of claim 10, wherein said first and second optical fibers each comprise distal ends, said distal ends each comprising an angled surface coated with a reflecting material.

14. The device of claim 13, wherein said first and second fibers are positioned so that light exits said distal end of said first optical fiber and enters said distal end of said second optical fiber.

15. The device of claim 1, wherein said device further comprises a housing which can be inserted into an artery of a living subject for in vivo measurement of nitric oxide.

16. The device of claim 1, wherein said nitric oxide-sensing compound is embedded in a polymeric material.

17. The device of claim 16, wherein said polymeric material is a fluorinated polymeric material permeable to nitric oxide.

18. The device of claim 1, wherein said device detects nitric oxide in vivo in the range of 0.001 µM to 10.0 µM.

19. A method of measuring an in vivo amount of nitric oxide in a subject, comprising calibrating the device of claim 1 with known concentrations of nitric oxide to generate a calibration equation, placing the device in a blood vessel of the subject, delivering light to the device, detecting light transmitted through the nitric oxide-sensing compound to generate an electrical signal, and processing the electrical signal with the calibration equation to calculate an in vivo amount of nitric oxide.

20. A device for measuring an in vivo amount of nitric oxide, comprising:

a housing;

a first optical fiber partially contained within said housing, said first optical fiber having distal and proximal ends, wherein said distal end of said first optical fiber comprises an angled surface comprising a reflective coating for delivering light;

a second optical fiber partially contained within said housing and positioned adjacent to said first optical fiber, said second optical fiber comprising an opening and having distal and proximal ends, wherein said distal end of said second optical fiber comprises an angled surface comprising a reflective coating for receiving light from said first optical fiber; and a nitric oxide-sensing compound, embedded in a polymer matrix in said opening of said second fiber, and positioned to receive light reflected by the reflective coating on the distal end of the second optical fiber.

21. The device of claim 20, wherein said first fiber comprises an opening containing a reference compound comprising a polymeric material.

22. The device of claim 21, wherein said polymeric material is light transparent.

23. The device of claim 21, wherein said polymeric material emits light.

24. A method for determining an in vivo amount of nitric oxide, comprising:

inducing a change in an optical property of a nitric oxide-sensing compound with in vivo nitric oxide; and detecting the change in the optical property to determine the in vivo amount of nitric oxide.

25. The method of claim 24, wherein said inducing step comprises delivering light to the nitric oxide-sensing compound; and said detecting step comprises collecting a portion of light that passes through the nitric oxide-sensing compound and analyzing the collected portion of light to determine the in vivo amount of nitric oxide.

26. The method of claim 24, wherein the inducing step includes inducing a change in the absorption spectrum of the nitric oxide-sensing compound.

27. The method of claim 26, wherein the change in the absorption spectrum is related to the in vivo amount of nitric oxide.

* * * * *

UNITED STATES PATENT AND TRADEMARK OFFICE
CERTIFICATE OF CORRECTION

PATENT NO.   : 5,582,170

DATED        : December 10, 1996

INVENTOR(S)  : Babs R. Soller

It is certified that error appears in the above-identified patent and that said Letters Patent is hereby corrected as shown below:

<u>In the Specification</u>

Col. 3, line 66, delete "*E.*" and insert therefor --*R.*--;

Col. 8, line 22, delete "supra" and insert therefor --<u>supra</u>--;

Col. 10, line 63, delete "1", and insert therefor (*1*); and

Col. 11, line 31, delete "supra" and insert therefor --<u>supra</u>--.

Signed and Sealed this

Eighth Day of May, 2001

*Attest:*

NICHOLAS P. GODICI

*Attesting Officer*   Acting Director of the United States Patent and Trademark Office